US00PP30326P2

(12) United States Plant Patent
Bagdasarian

(10) Patent No.: US PP30,326 P2
(45) Date of Patent: Apr. 2, 2019

(54) STRAWBERRY PLANT NAMED 'CAMILA'

(50) Latin Name: *Fragaria x ananassa*
Varietal Denomination: Camila

(71) Applicant: Jimmy Haig Bagdasarian, Santa Cruz, CA (US)

(72) Inventor: Jimmy Haig Bagdasarian, Santa Cruz, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 15/732,748

(22) Filed: Dec. 23, 2017

(51) Int. Cl.
*A01H 5/08* (2018.01)

(52) U.S. Cl.
USPC ..... Plt./209

(58) Field of Classification Search
USPC ..... Plt./209
See application file for complete search history.

(56) References Cited

U.S. PATENT DOCUMENTS

| | | | |
|---|---|---|---|
| PP22,472 | P3 | 1/2012 | Bagdasarian |
| PP26,974 | P3 | 7/2016 | Bagdasarian |
| PP27,034 | P3 | 8/2016 | Bagdasarian |
| PP27,190 | P3 | 9/2016 | Bagdasarian |

*Primary Examiner* — Annette H Para
(74) *Attorney, Agent, or Firm* — Phase M Legal

(57) ABSTRACT

A new and distinct variety of strawberry plant (*Fragaria* X *ananassa*) named 'Camila.' This new short-day strawberry variety is characterized by a vigorous plant which produces mostly long conical fruit with a good sweet strawberry flavor, and a very desirable lighter red exterior and interior color. The variety, while short-day, is fully remontant in cool coastal environments of California.

6 Drawing Sheets

Latin name of the genus and species of the plant claimed: Botanical classification: *Fragaria* x *ananassa.*

Variety denomination: The new strawberry variety denomination is 'Camila.'

BACKGROUND OF THE INVENTION

Field of Invention

The present invention relates to a new and distinct strawberry variety named 'Camila.' This new short-day variety is the result of a controlled cross in an ongoing breeding program by the inventor, Jimmy Bagdasarian, in 2009. The variety is botanically known as *Fragaria* X *ananassa*. The primary market of this variety is for the fresh market sales of the fruit. 'Camila' produces large, conical berries, which are firm, have good flavor and a light red color.

Comparison with Parent Varieties

The controlled cross which produced 'Camila' was the result of a cross in 2009 between a strawberry variety used as a female parent designated '1D12' (an unreleased and non-patented proprietary variety,) and a strawberry variety used as the male pollen parent designated 'Sweet Ann,' (U.S. Plant Pat. No. 22,472).

The characteristics of the female parent '1D12' are: short-day variety with very firm fruit which are light in color and can be a bit irregular in shape. The plant exhibits medium vigor with lighter green leaves.

The male pollen parent 'Sweet Ann' has the following characteristics: day-neutral with an open plant density and high vigor plant; leaves are medium glossy with little to no blistering; fruit are very large, conical, and sweet, with a glossy medium red color both interior and exterior, often with a white shoulder near the calyx.

'Camila,' is a short-day plant, unlike its male parent 'Sweet Ann.' It has intermediate vigor to its parents with that more closely aligning the more vigorous 'Sweet Ann' in nature. It has firmer fruit than that of the pollen parent 'Sweet Ann,' but not quite as firm as that of the female parent '1D12.' The fruit of 'Camila' is quite uniform like that of 'Sweet Ann,' and unlike the sometimes misshapen '1D12.'

The cross made to create 'Camila' was carried out in Santa Cruz, Calif., USA. Pollen taken from 'Sweet Ann' was placed onto a flower with male parts removed on '1D12' and then covered so that no other pollen could contaminate the procedure.

Once the strawberries developed from this cross, they were harvested and the resulting seed was extracted and germinated in a greenhouse in Redding, Calif., USA. The resulting seedlings were transplanted to Shastina, Calif. in 2010, grown out for an additional period and allowed to propagate asexually through runners. Clones were then harvested and planted in breeding plots in fruiting fields in mid-October in: Oxnard, Calif. (Ventura County); and Watsonville, Calif. (Monterey County). The selection of the new variety was first made in Watsonville, Calif., and given the designation '23K18' in 2011. This selection was later named 'Camila.'

The variety was further propagated asexually by runners (stolens) in breeding plots in: Macdoel, Calif. (Siskiyou County); and Manteca, Calif. (San Joaquin County).

The new variety has also been "meristemed." Small pieces of plant material of approximately 0.5 mm in diameter and consisting of the undifferentiated meristem tissue and one or two leaf primordia were removed from the buds on crowns of young daughter plants, then placed on nutrient medium, and new plants were grown from them. Planting stock from the "meristemed" plants are growing in a screen-house located in Redding, Calif. These propagules of 'Camila' are identical to the original plant in all distinguishing characteristics. The propagation has been monitored throughout the process, and all traits disclosed here remain fixed and true to type through successive generations of asexual reproduction.

SUMMARY OF THE INVENTION

'Camila' is a short-day variety exhibiting the following combination of characteristics, which have been observed repeatedly, and which distinguish this strawberry plant as a new and distinct variety:

1. The variety produces large sized fruit;
2. The fruit is mostly a long conic shape;
3. The fruit is attractive, having a glossy medium red exterior and light red interior;
4. The fruit is sweet tasting, with good flavor;
5. The variety produces a high volume of fruit;
6. The plants of the variety are vigorous and maintain a fairly open and upright architecture;
7. The variety is fully remontant in cool coastal environments.

'Camila' fruit is larger than that of its female parent '1D12,' but smaller than that of its paternal parent 'Sweet Ann.' The ripening pattern of 'Camila' is more desirable than that of 'Sweet Ann' as it ripens more fully to the top, whereas in certain conditions, 'Sweet Ann' does not color all the way to the calyx. While the fruit of 'Camila' are of similar firmness to '1D12,' it is much firmer than that of 'Sweet Ann.' Another good quality of 'Camila' is that it has a lighter, medium red color which is more preferred by shippers of fresh strawberries, because darker colored berries are perceived as being overly ripe.

BRIEF DESCRIPTION OF THE DRAWINGS

The accompanying color photographs, identified as FIGS. 1 through 6, show the appearance of typical specimens of the new strawberry variety 'Camila.' These figures depict the colors as nearly true as it is reasonably possible given differences in color illustrations of this character. Accordingly, color in the photographs may differ slightly from the colors discussed in the botanical description. The photographs of the depicted plant, plant parts, and fruit of 'Camila' (previously designated as '23K18') were taken in October/November of 2017.

DETAILED BOTANICAL DESCRIPTION OF THE PLANT

Figure 1:
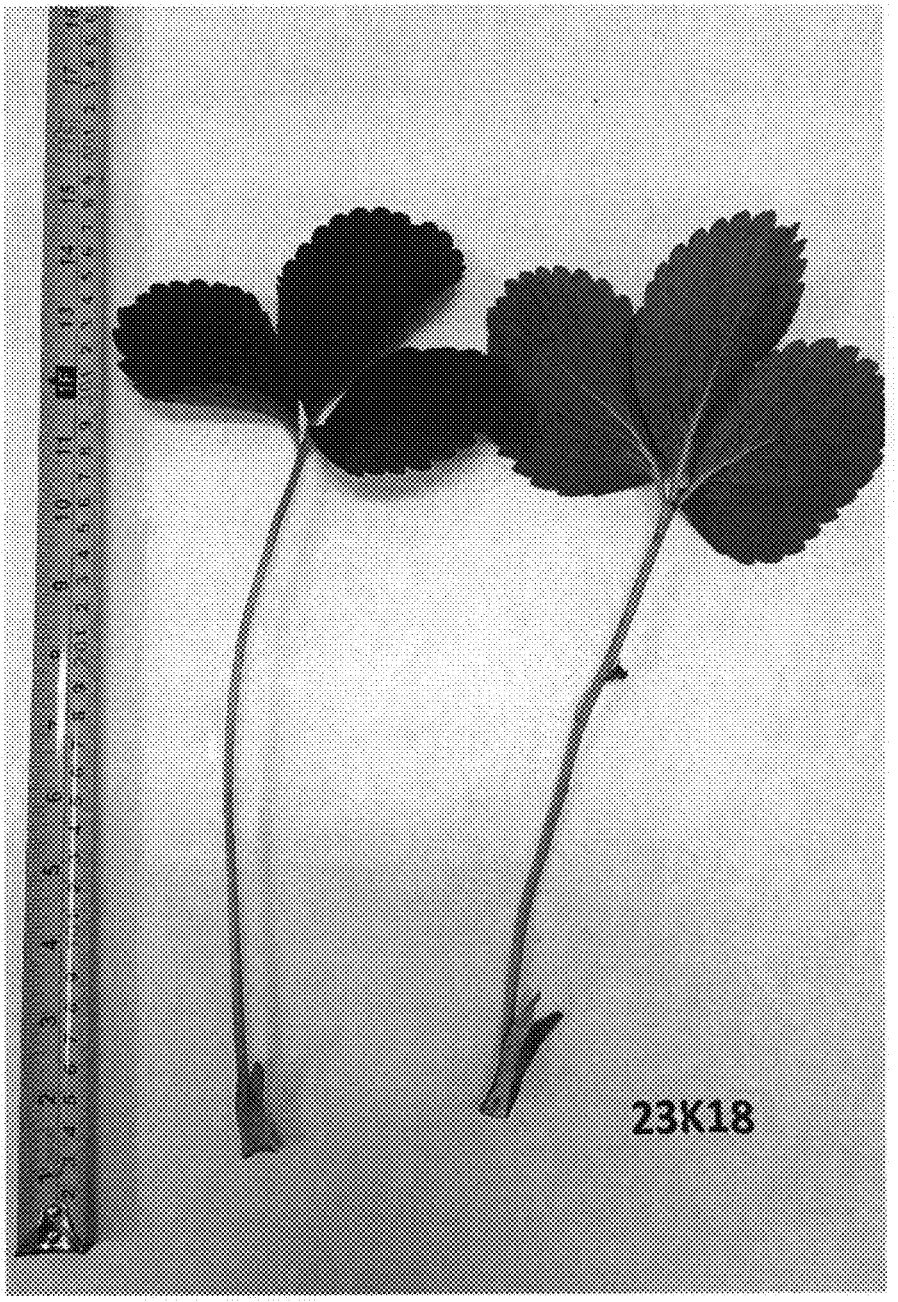
FIG. 1 shows the top and bottom of a typical leaf and petiole structures of '23K18,' now denominated as 'Camila.'
Figure 2:
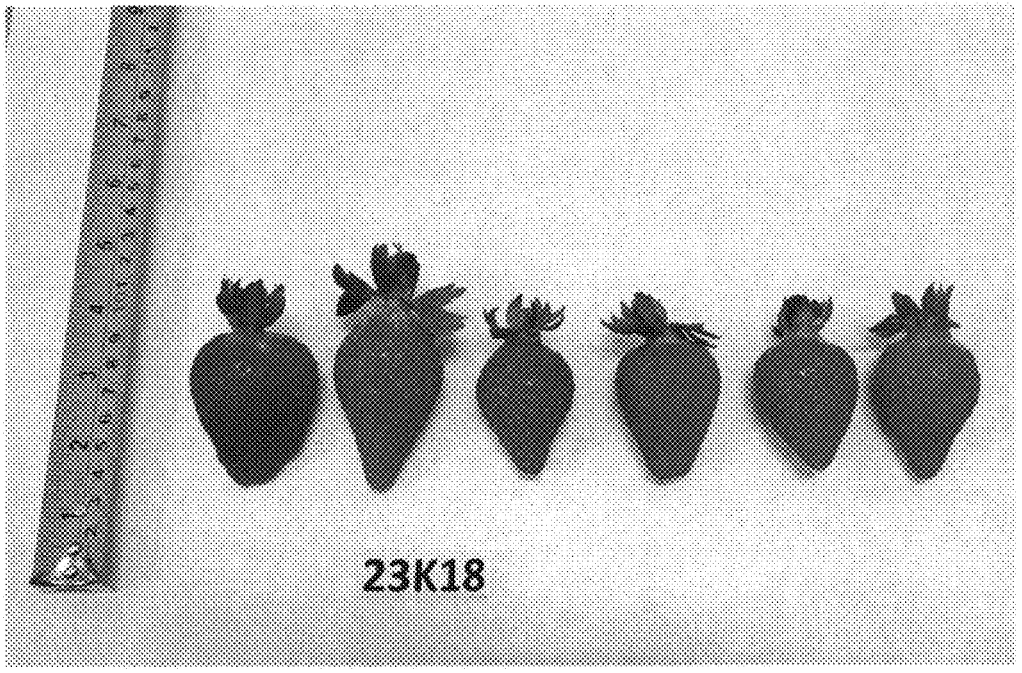
FIG. 2 shows a selection of late-season fruit.
Figure 3:
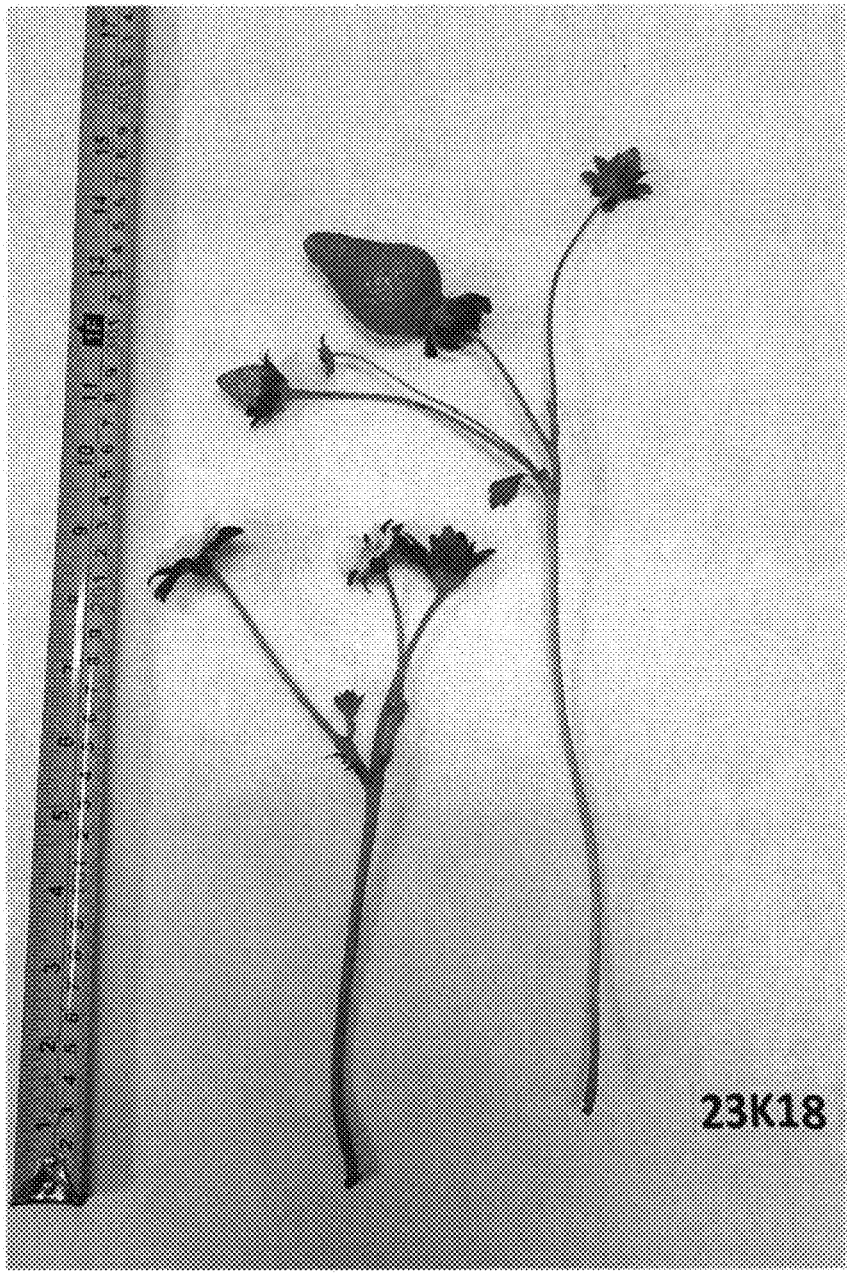
FIG. 3 shows two typical inflorescences.
Figure 4:
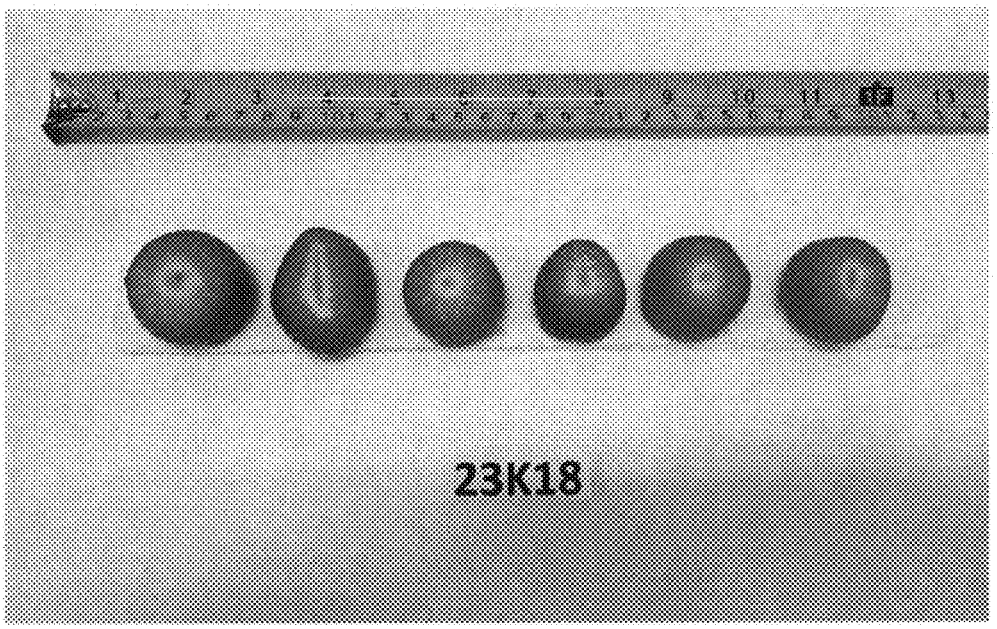
FIG. 4 shows a transverse cross-section of typical fruit, internal coloration and core size.
Figure 5:
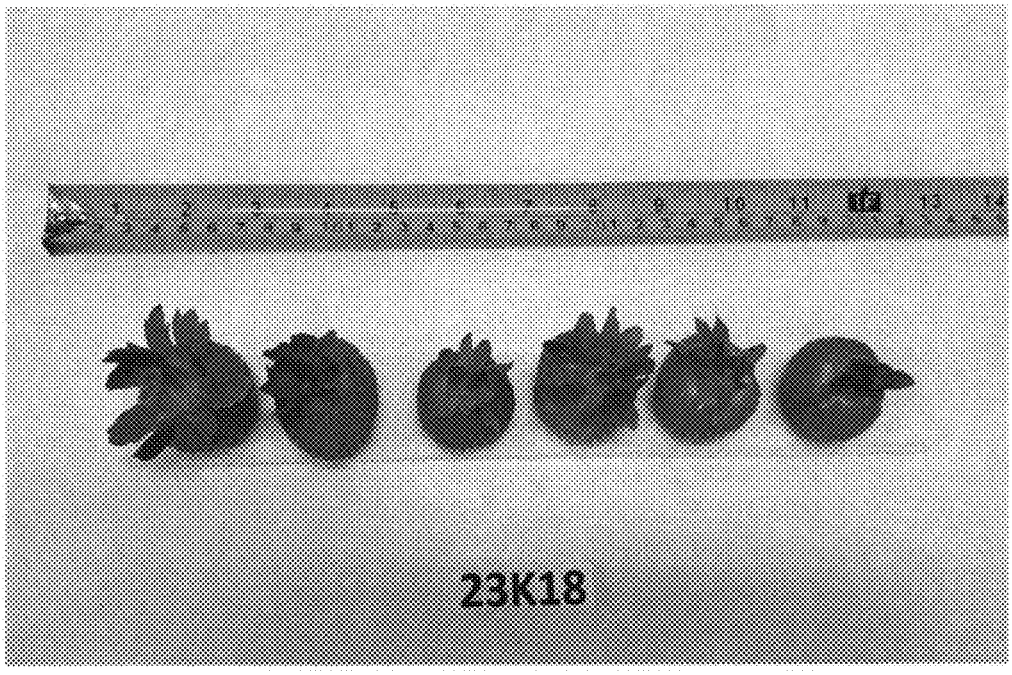
FIG. 5 shows calyx shape and position in relationship to fruit in late season; and, FIG. 6 shows typical late season plants in a fruiting field.
Figure 6:
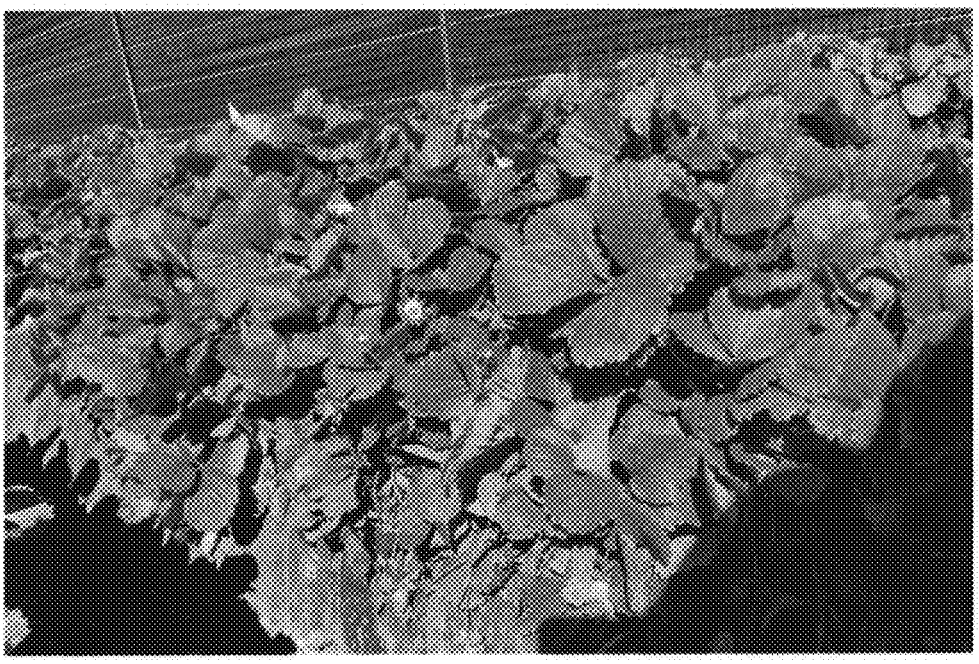

'Camila' is a new and distinct variety of strawberry (*Fragaria* X *ananassa*). It is the result of a cross between its female parent, '1D12,' and 'Sweet Ann.' The female parent '1D12,' is a short-day plant, and the male parent 'Sweet Ann' is a day neutral variety. While 'Camila' is short-day, it is remontant (day-neutral tendencies) in cool coastal environments, and partially remontant in warmer inland environments, but blooms only once in a high elevation nursery, consistent with a short-day variety. The plants of the new variety are vigorous and produce multiple crowns early after planting. 'Camila' exhibits several characteristics which are improvements over one or both of its parent varieties, and other known cultivars. The characteristics of 'Camila' were observed in plants in late season. These characteristics and comparisons with other cultivars are discussed below.

The fruiting pattern of 'Camila' is similar to that of 'Sweet Ann.' The fruit size of 'Camila' is uniformly large, slightly smaller than the fruit produced by 'Sweet Ann,' but larger than the fruit produced by '1D12.' This slightly smaller size of fruit of 'Camila' provides an advantage in packaging fruit, where fruit too large can be damaged, but fruit too small can take longer to pick, and is less marketable.

The fruit of 'Camila,' the female parent '1D12,' and the male parent 'Sweet Ann' produce long conic fruit, however the fruit of '1D12' is not as uniformly smooth. The fruit of 'Camila' ripens more throughout the fruit rather than from the tip to the shoulders of the berry, resulting in a more uniform red color over the whole fruit when fully ripe. In contrast, the shoulders of the fruit of "Sweet Ann' are the last portion to ripen, and in some cases do not fully turn red. The fruit of 'Camila' is nearly absent of any creases and is smoother than that of 'Sweet Ann' and '1D12.' While '1D12 is slightly firmer, 'Camila' is still firm, and in fact is firmer than 'Sweet Ann.'

The data set forth for 'Camila' in Table 1 was collected in October/November in 2017 from plants grown in a test plot in Moss Landing, Monterey County, Calif. Color terminology where noted is in accordance with the Pantone Color Formula Guide GP 1201.

TABLE 1

Detailed Description of Characteristics of 'Camila'

| | |
|---|---|
| SPECIFICATION: | |
| Genus/Species | *Fragaria* X *ananassa* |
| Market Name | Strawberry |
| PARENTS: | |
| Female | Proprietary variety '1D12' (Unpatented) |
| Male | 'Sweet Ann' (U.S. Plant Pat. No. 22,472). |
| PLANT: | |
| Type | Short Day. |
| Growth Habit | Semi-upright. |
| Foliage density | Dense. |
| Vigor | High. |
| Height | Average: 39.2 cm; range: 34 cm to 43 cm. |
| Width | Average: 60.1 cm; range: 47 cm to 68 cm. |
| Crowns | Multiple crowns produced early after planting. |
| Disease tolerance | Test plots from Cal Poly showed susceptibility to *Macrophomina phaseolina* (Crown rot) but a moderate tolerance to *Verticillium dahliae*. |
| LEAF: | |
| Width | Average: 151 cm; range: 115 cm to 200 cm. |

TABLE 1-continued

| Detailed Description of Characteristics of 'Camila' | |
|---|---|
| Color | Adaxial surface: green 357 C.<br>Abaxial surface: green 371 U. |
| Pubescens | Medium density. |
| Inter-vein blistering | Low-moderate. |
| Glossiness | Medium. |
| Variegation | None. |
| TERMINAL LEAFLET: | |
| Length | Average: 90.1 mm;<br>range: 70 mm to 115 mm. |
| Width | Average: 82.6 mm;<br>range: 70 mm to 100 mm. |
| Ratio length to width | 1.09. |
| Margins | Serrate to crenate. |
| Leaf shape | Orbicular. |
| Base shape | Acute. |
| Cross-section shape | Concave. |
| PETIOLE: | |
| Pubescens | Medium density; direction: perpendicular. |
| Petiole color | Green 381 U. |
| Petiole length | Average. 26.5 cm;<br>Range: 22.5 cm to 30.2 cm. |
| Petiole diameter | Average: 3.25 mm;<br>Range: 2.67 mm to 3.57 mm. |
| STIPULE: | |
| Anthocyanin coloration | Present, moderate. |
| Length | Average: 30.3 mm;<br>Range: 19 mm to 42 mm. |
| Width | Average: 11.1 mm;<br>Range: 9 mm to 13 mm. |
| STOLEN: | |
| Anthocyanin coloration | Present. |
| Pubescens | Low to medium; upward to perpendicular direction. |
| Diameter | Average: 3.1 mm;<br>Range: 1.78 mm to 3.57 mm. |
| INFLORESCENCE: | |
| Flowering time | Moderately early. |
| Position | At, or slightly below the canopy. |
| Number of blooms | Average: 4.4; Range: 3 to 9. |
| Length | Average: 31.5 cm;<br>Range: 27 cm to 36 cm. |
| Flower | Average dictilieter: 29.8 mm;<br>Range: 26 mm to 35 mm. |
| Petal arrangement | Mostly overlapping. |
| Petal number | Average: 5.5; Range: 5 to 7. |
| Petal length | Average: 10.9 mm;<br>Range: 10 mm to 12 mm. |
| Petal width | Average: 11.5 mm;<br>Range: 10 mm to 13 mm. |
| Ratio length to width | 0.95. |
| Petal color | Bright white 11-0601 TPX, but can transition to 1905 U when mature. |
| Calyx | Slightly larger to much larger than the corolla. |
| Calyx color | Adaxial surface: green 3435 C.<br>Abaxial Surface: green 371 U. |
| Stamens | Average number: 29.3;<br>Range: 25 to 32. |
| Pedicel | Attitude of hairs is perpendicular. |
| FRUIT | |
| Bearing | Remontant in cool coastal environments; partial remontance inland. |
| Shape | Well shaped, long conical. |
| Size | Seasonal average: 23 g. |

TABLE 1-continued

| Detailed Description of Characteristics of 'Camila' | |
|---|---|
| Achenes | Approximately level with the fruit surface. |
| Glossiness | Strong. |
| External color | Red 186 C. |
| Internal color | Flesh (excluding core): Red 186 U. |
| Evenness of external color | Nearly to the top of the berry when fully ripe. |
| Width of band at top devoid of achenes | Small. |
| Fruit center | Some hollowness. |
| Yield | Average grams per plant: 1857 g. |
| Firmness | Firm, firmer than parent and cultivar 'Sweet Ann.' |
| % Brix | Average: 8.6; Range: 7.8-9.7. |

The comparison statistics set forth in the following Tables are with respect to characteristics observed in the late season of 'Camila.' All measurements for 'Camila' were taken in Moss Landing, Calif. in 2017. In Tables 2 and 3, the characteristics of 'Camila' are compared with the varieties 'Sweet Ann' and 'Lucia' (U.S. Plant Pat. No. 26,974) historical data. Color identifications where noted are in accordance with the Pantone Color Formula Guide GP 1201.

Plants and Foliage

The vigor of 'Camila' is similar to that of 'Sweet Ann,' while 'Sweet Ann' has a more open architecture. The plant spread of 'Camila' is quite a bit larger than the compared varieties, but has a leaf spread that is smaller on average. The petiole diameter of 'Camila' is also smaller on average than that of the compared varieties.

TABLE 2

Foliar Characteristics of 'Camila' Compared to 'Lucia' and 'Sweet Ann'

| Foliar Characteristics | | Cultivar 'Camila' | 'Lucia' | 'Sweet Ann' |
|---|---|---|---|---|
| Plant height (mm) | Average | 392 | 391 | 380 |
| | Range | 340-430 | 292-490 | 290-480 |
| Plant spread (mm) | Average | 601 | 472 | 420 |
| | Range | 470-680 | 430-550 | 330-510 |
| Leaf width (mm) | Average | 151 | 195 | 165 |
| | Range | 115-200 | 165-220 | 130-195 |
| Mid-ticr leaflet length (mm) | Average | 90 | 103 | 88 |
| | Range | 70-115 | 82-116 | 72-105 |
| Mid-tier leaflet width (mm) | Average | 83 | 91 | 67 |
| | Range | 64-100 | 73-102 | 52-88 |
| Petiole length (mm) | Average | 265 | 268 | 220 |
| | Range | 225-302 | 230-335 | 150-280 |
| Petiole diameter (mm) | Average | 3.25 | 4.48 | 3.74 |
| | Range | 2.67-3.78 | 3.70-5.80 | 3.01-4.29 |
| Number of leaflets per leaf | | 3 | 3 | 3 |
| Leaf convexity | | Concave | Slight concave | Slight concave |
| Shape of leaflet base | | Acute | Rounded to obtuse | Obtuse |
| Leaf pubescence | | Medium | Medium | Medium |
| Petiole pubescence | | Medium | Medium | Medium |
| Direction | | Perpendicular | Perpendicular | Perpendicular |
| Stipule length (mm) | Average | 30.3 | 35.7 | Not available |
| | Range | 19-42 | 30-40 | |
| Stipule anthocyanin coloration | | Yes | Yes | Yes-weak |
| Leaf margins | | Serrate to crenate | Serrate to crenate | Commonly crenate |

TABLE 2-continued

Foliar Characteristics of 'Camila' Compared to 'Lucia' and 'Sweet Ann'

| Foliar Characteristics | Cultivar 'Camila' | 'Lucia' | 'Sweet Ann' |
|---|---|---|---|
| Leaf color adaxial surface | 357 C | 364 U | 364 U |
| Leaf color abaxial surface | 371 U | 363 U | 370 U |
| Petiole color | 381 U | 366 U | 383 U |
| Leaf surface blistering | Low-medium | Medium | Very weak |
| Leaf surface glossiness | Medium | High | Medium |

Flowers and Fruit

'Camila' is a short-day variety as it blooms only once in high-elevation nurseries. It is, however, remontant in cool, coastal environments, and partially remontant in warmer inland environments. While 'Lucia' tends to have a steady number of 5 petals, 'Camila' fluctuates from 5 to 7 petals; more than that of 'Sweet Ann' (5-6 petals). The mature petals of 'Camila' have occasionally been seen to transition from bright white to a pink color in certain conditions, whereas this does not happen in 'Lucia' or in 'Sweet Ann.'

The external color of 'Camila' fruit is slightly darker than that of 'Lucia,' but similar in color to 'Sweet Ann.' The fruit of 'Camila' has excellent fresh-market qualities, including: good conic shape and large size, lighter red color, good firmness, and good flavor.

In Table 3, comparative data for flower and fruit characteristics for 'Camila,' 'Lucia,' and 'Sweet Ann' are set forth.

TABLE 3

Flower and Fruit Characteristics of 'Camila' Compared to 'Lucia' and 'Sweet Ann'

| Characteristic | | Cultivar 'Camila | 'Lucia' | 'Sweet Ann' |
|---|---|---|---|---|
| Petal number | Average | 5.5 | 5 | 5.4 |
| | Range | 5-7 | 5 | 5-6 |
| Petal length (mm) | Average | 10.9 | 12.44 | 11.21 |
| | Range | 10-12 | 10.6-14.3 | 9.2-13 |
| Petal width (mm) | Average | 11.5 | 11.86 | 11.1 |
| | Range | 10-13 | 10-13 | 9-13 |
| Position of flower (relative to canopy) | | Most exposed, some below | mostly exposed | most exposed, some even |
| Pedicel length (mm) | Average | 315 | 430 | 330 |
| | Range | 270-360 | 380-540 | 240-420 |
| Sepal color | Adaxial | 3435 C | 364 U | 364 U |
| | Abaxial | 371 U | 371 U | 370 U |
| Corolla diameter (mm) | Average | 29.8 | 28.2 | 30.3 |
| | Range | 26-35 | 23.5-34 | 27-33 |
| Fruit color | External | 186 C | 1788 C | 185 C |
| | Internal | 186U | 179C | 1788C |

Leaf samples from 'Camila,' along with three other patented selections from the breeding program including 'Lucia,' 'Scarlet,' (U.S. Plant Pat. No. 27,034) and 'Ruby June' (U.S. Plant Pat. No. 27,190) were submitted to a lab for allelic fingerprint comparison to over two hundred other varieties of strawberry in its data base. The allelic fingerprint analysis establishes that 'Camila' is distinct and unique compared to the lab's large database of allelic fingerprints. Table 4 sets forth test results of three markers which differentiate 'Camila.'

TABLE 4

Allelic Fingerprint Analysis

| Cultivar | Marker 1 | Marker 2 | Marker 3 |
|---|---|---|---|
| 'Camila' | 204, 206, 224, 229 | 190, 232 | 121, 124, 130 |
| 'Lucia' | 202, 204, 206, 229 | 188, 216, 232 | 121, 124, 130, 136 |
| 'Scarlet' | 204, 206, 214, 229 | 173, 190, 232 | 121, 130 |
| 'Ruby June' | 206, 224, 229 | 188, 190, 216, 232 | 121, 130 |

Performance

Performance with respect to fruit size, yield and appearance for 'Camila' was assessed by making comparisons with several other varieties in the breeding program, including 'Sweet Ann,' 'Lucia,' 'Ruby June,' and 'Scarlet.' All the plants for this trial were initially grown at a high elevation nursery in Macdoel, Siskiyou County, Calif. Plants of 'Camila' and the comparison varieties were then planted and evaluated in a test plot in Moss Landing, Monterey County, Calif. in the end of 2016, through 2017.

Of the varieties tested, 'Camila' had the second highest average seasonal yield (1,857 grams/plant), where it was only outperformed by 'Sweet Ann' (2,003 grams/plant). While 'Camila' had smaller average fruit weight though the season, it averaged the same as that of 'Ruby June' for fruit size.

The fruit of 'Camila' was rated based upon commercial appeal on a scale of 1 (worst) to 5 (best) along with several other varieties. 'Camila' had a high score of 4.0 (tied with 'Sweet Ann') which was better than that of both 'Ruby June' (3.75) and 'Scarlet' (3.5). Only 'Lucia' outperformed 'Camila' in this comparison with a rating of 4.5, due to it near uniform berries.

Table 5 shows the fruit performance of 'Camila' as compared to 'Sweet Ann,' 'Lucia,' 'Ruby June,' and 'Scarlet.'

TABLE 5

Comparison of Performance of 'Camila' to Other Varieties

| Cultivar | Seasonal Yield grams/plant | Seasonal Average berry weight grams/berry | Appearance Score Rating 5 = Best |
|---|---|---|---|
| 'Camila' | 1,857 | 23 | 4.0 |
| 'Sweet Ann' | 2,003 | 31 | 4.0 |
| 'Ruby June' | 1,597 | 23 | 3.75 |
| 'Lucia' | 1,584 | 25 | 4.5 |
| 'Scarlet' | 1,460 | 27 | 3.5 |

I claim:

1. A new and distinct strawberry plant named 'Camila' as described and illustrated by the characterizations set forth above.

* * * * *